United States Patent [19]
Katoh et al.

[11] Patent Number: 5,908,757
[45] Date of Patent: Jun. 1, 1999

[54] ANTIBODY REAGENT FOR DETECTING DISSECTING AORTIC ANEURYSM AND USES THEREOF

[75] Inventors: Hirohisa Katoh, Choshi; Ryozo Nagai, Maebashi, both of Japan

[73] Assignee: Yamasa Corporation, Chiba-ken, Japan

[21] Appl. No.: 08/817,810

[22] PCT Filed: Oct. 24, 1995

[86] PCT No.: PCT/JP95/02180

§ 371 Date: Apr. 10, 1997

§ 102(e) Date: Apr. 10, 1997

[87] PCT Pub. No.: WO96/12507

PCT Pub. Date: May 2, 1996

[30] Foreign Application Priority Data

Oct. 25, 1994 [JP] Japan ................................ 6-284073

[51] Int. Cl.$^6$ ...................... G01N 33/543; G01N 33/577; G01N 33/68
[52] U.S. Cl. .................... 435/7.94; 435/7.1; 435/7.92; 436/518; 436/528; 436/548; 436/811; 530/388.2; 530/391.1; 935/110
[58] Field of Search ............................ 435/7.1, 7.9, 7.92, 435/7.94, 70.21, 172.2, 975, 332, 337; 436/518, 524, 528, 534, 548, 808, 811; 935/104, 106, 110; 530/388.2, 389.1, 391.1

[56] References Cited

FOREIGN PATENT DOCUMENTS

| | | |
|---|---|---|
| 0 131 834 | 1/1985 | European Pat. Off. . |
| 0 163 041 | 12/1985 | European Pat. Off. . |
| 0 443 511 A2 | 8/1991 | European Pat. Off. . |
| 0 465 652 A1 | 1/1992 | European Pat. Off. . |
| 60-201260 | 10/1985 | Japan . |
| 2-219596 | 9/1990 | Japan . |
| 5-176790 | 7/1993 | Japan . |
| 89/12467 | 12/1989 | WIPO . |
| 90-11520 | 10/1990 | WIPO . |

OTHER PUBLICATIONS

Sartore et al., 1989. Myosin heavy–chain isoforms in human smooth muscle. Eur. J. Biochem. 179: 79–85.

Mohammad et al., 1989. The distribution of heavy–chain isoforms of myosin in airways smooth muscle from adult and neonate humans. Biochem. J. 260: 421–426.

Schneider et al., 1985. Localization and topography of antigenic domains within the heavy chain of smooth muscle myosin. J. Cell Biol. 101: 66–72.

Chemical Abstract of JP 5–148160, Chem Abstracts 119: 383, #119:176770r.

Toru Suzuki et al., "Novel Biochemical Diagnostic Method for Aortic Dissection", Biochemical Diagnosis of Aortic Dissection, Circulation, vol. 93, No. 6, pp. 1244–1249, Mar. 15, 1996.

Hirohisa Katoh et al., "A Novel Immunoassay of Smooth Muscle Myosin Heavy Chain in Serum", Journal of Immunological Methods, vol. 185, pp. 57–63, 1995.

*Primary Examiner*—James C. Housel
*Assistant Examiner*—James L. Grun
*Attorney, Agent, or Firm*—Wenderoth, Lind & Ponack, L.L.P.

[57] ABSTRACT

By measuring smooth muscle myosin heavy chain in the blood of a patient using an antibody to the smooth muscle myosin heavy chain, dissecting aortic aneurysm can be diagnosed very easily and rapidly without any special equipment.

6 Claims, 8 Drawing Sheets

CALIBRATION CURVE

EFFECT OF SURFACTANT

EFFECT OF SURFACTANTS

EFFECT OF SURFACTANTS

EFFECT OF SURFACTANTS

5,908,757

ANTIBODY REAGENT FOR DETECTING DISSECTING AORTIC ANEURYSM AND USES THEREOF

BACKGROUND OF THE INVENTION

1. Field

The present invention relates to an antibody reagent for detecting dissecting aortic aneurysm (recently also called aortic dissection) which comprises an antibody to a smooth muscle myosin heavy chain, and use of the antibody reagent.

2. Description of Related Art

Dissecting aortic aneurysm is a disease with severe chest pains and is caused by disruption of the aortic media by blood entering through a laceration of the luminal vascular wall. Dissecting aortic aneurysm is caused in aorta in most cases but is caused also in branches in some cases. As causes for the disease, there are suggested not only the degeneration and weakening of the intima (e.g. cystic medionecrosis and arterio-sclerosis) but also the extension of aorta, hypertension, etc.

A typical example of disease with chest pains is acute myocardial infarction. Acute myocardial infarction may be diagnosed without much difficulty through electrocardiograph change or biochemical blood testing. By contrast, in the case of dissecting aortic aneurysm, a specific change is hardly observed in an electrocardiograph or blood testing in spite of the high lethality of this disease. Therefore, diagnosis of this disease requires extreme care.

As a method for diagnosis of dissecting aortic aneurysm, echo examination, CT (X-rays computed tomography), DSA (digital subtraction angiography), MRI (magnetic resonance imaging), etc. have been attempted and have produced rather good results (Common Disease Series 4: Angina Pectoris·Myocardial Infarction, pp. 310–313, Nankodo K. K.). All of these methods, however, require special equipment, and hence are not always satisfactory as a method for use in an urgent examination wherein the method is required to be always able to be carried out anywhere.

Accordingly, the present invention is mainly intended to provide a method for detecting dissecting aortic aneurysm which is applicable to an urgent examination, and a reagent for use in the method.

SUMMARY OF THE INVENTION

The present inventors conducted detailed researches with the expectation that, in the cases of a disease associated with blood vessel disturbance such as dissecting aortic aneurysm, a substance constituting the blood vessel is released into blood. Consequently, the present inventors concluded that the blood vessel disturbance can be diagnosed by detecting smooth muscle myosin heavy chain which is a main protein constituting the blood vessel.

Since smooth muscle myosin heavy chain is biochemically different from skeletal muscle myosin heavy chain, cardiac muscle myosin heavy chain and non-muscle myosin heavy chain, it is relatively easy to obtain an antibody specific for smooth muscle myosin heavy chain. Therefore, an antibody to smooth muscle myosin heavy chain was prepared, whereby there has been established an assay system which enables detection of smooth muscle myosin heavy chain in blood. The smooth muscle myosin heavy chain levels in the sera of healthy individuals were measured by this assay system and found to be low. On the other hand, as a result of measurement in the sera of patients with dissecting aortic aneurysm, there were observed significantly higher smooth muscle myosin heavy chain levels which clearly reflect the clinical symptoms of the patients. Thus, it was confirmed that measuring smooth muscle myosin heavy chain in blood is useful for detecting dissecting aortic aneurysm, whereby the present invention has been accomplished.

Accordingly, the present invention relates to an antibody reagent for detecting dissecting aortic aneurysm which comprises an antibody to smooth muscle myosin heavy chain.

The present invention also relates to a kit for detecting dissecting aortic aneurysm which comprises an antibody reagent to smooth muscle myosin heavy chain and a washing solution containing a surfactant.

The present invention further relates to a method for detecting dissecting aortic aneurysm which comprises measuring smooth muscle myosin heavy chain in a sample, and detecting dissecting aortic aneurysm on the basis of the value obtained.

The present invention still further relates to use of an antibody to smooth muscle myosin heavy chain for detecting dissecting aortic aneurysm.

Figure 1:
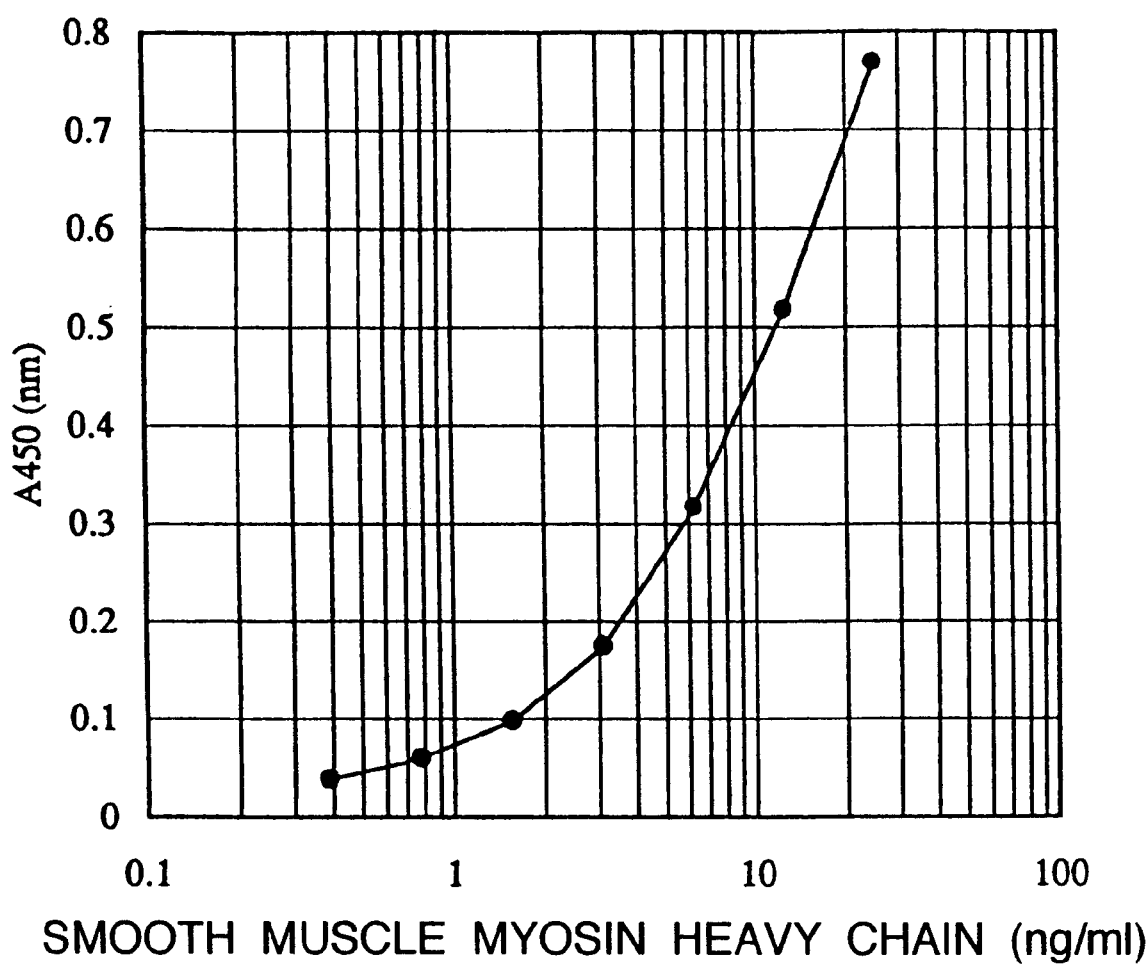
FIG. 1 shows a calibration curve.
Figure 2:
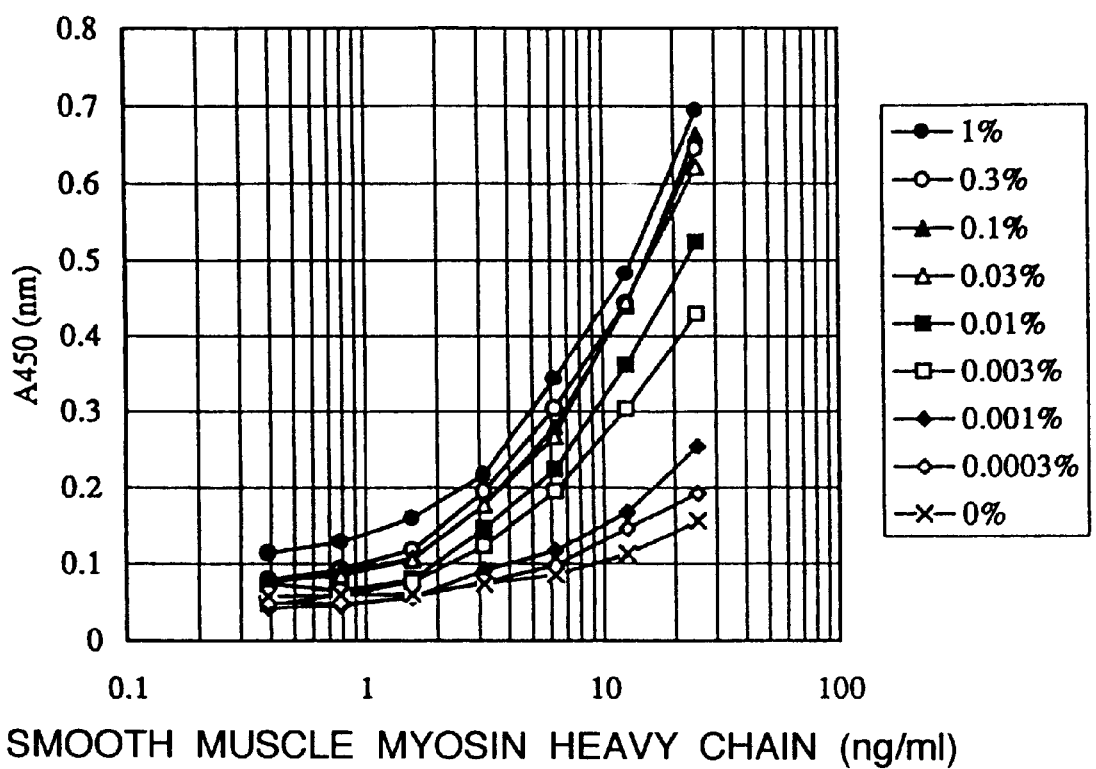
FIGS. 2 to 7 show the results of investigating the effects of surfactants.

DESCRIPTION OF THE PREFERRED EMBODIMENTS (1) Antibody reagent

The antibody reagent of the present invention is used in a method for detecting dissecting aortic aneurysm which comprises measuring smooth muscle myosin heavy chain in a test sample according to immunoassay, and detecting dissecting aortic aneurysm on the basis of the value obtained. Therefore, the antibody reagent of the present invention comprises at least an antibody specific for smooth muscle myosin heavy chain.

The antibody used in the antibody reagent of the present invention may be either polyclonal or monoclonal so long as it binds specifically to smooth muscle myosin heavy chain. The antibody is not particularly limited and may be a well-known one. In particular, an antibody having a low cross-reactivity with other myosins is preferably used. Specifically, smooth muscle myosin heavy chain in a sample can be specifically measured by the use of such a monoclonal antibody having less than 3% cross-reactivity with other myosins, preferably less than 1%, as is described in Examples described hereinafter.

Such a monoclonal antibody can be easily prepared by properly applying conventional methods as described in Examples described hereinafter [see, for example, Japanese Biochemical Association, "Men-eki Seikagaku Kenkyuho (Zoku Seikagaku Jikken Koza 5)", pp. 1–88 (1986); Biochemistry, 27, 3807–3811 (1988); Eur. J. Biochem., 179, 79–85 (1989); J. Mol. Biol., 198, 143–157 (1987); J. Biol. Chem., 264, 9734–9737 (1989); J. Biol. Chem., 264, 18272–18275 (1989); J. Biol. Chem., 266, 3768–3773 (1991); Circulation, 88, 1804–1810 (1993)].

As the antibody used in the antibody reagent of the present invention, an antibody itself may be used. Preferably, an active antibody fragment thereof is used, because the fragment can prevent non-specific adsorptions thereto. As the active antibody fragment, there may be used any of various active antibody fragments retaining characteristics of the antibody, such as F(ab')2, Fab' and Fab. These active fragments may be prepared according to conventional methods including one comprising limited degradation of a purified antibody with a protease such as papain, pepsin and trypsin [see, for example, Japanese Biochemical Association, "Men-eki Seikagaku Kenkyuho (Zoku Seikagaku Jikken Koza 5)", p. 89 (1986)].

As the antibody reagent, a dissolved antibody or a freeze-dried antibody may be used. If necessary, a modified antibody in a form suitable for a measurement system (e.g. an immobilized anitibody or a labeled antibody) may be used as the antibody reagent.

The antibody modification may be carried out according to conventional methods. In more detail, as a material for a carrier for preparing the immobilized antibody, there may be exemplified synthetic organic high-molecular weight compounds such as poly(vinyl chloride)s, polystyrenes, styrene-divinylbenzene copolymers, styrene-maleic anhydride copolymers, nylons, poly(vinyl alcohol)s, polyacrylamides, polyacrylonitriles, polypropylenes, and poly(methylene methacrylate)s polysaccarides such as dextran derivatives (e.g. Sephadex), agarose gels (e.g. Sepharose and Bio-Gel), and celluloses (e.g. paper disc and filter paper); and inorganic high-molecular weight compounds such as glass, silica gel, and silicones. These materials may have one or more functional groups (e.g. amino group, aminoalkyl group, carboxyl group, acyl group and hydroxyl group) introduced thereinto. The material for the carrier preferably has a marked protein-binding ability.

As to the shape of the carrier, there may be exemplified flat plate-like carriers (e.g. microtiter plates and discs), granular carriers (e.g. beads), tubular carriers (e.g. test tubes), fibrous, filmy or particulate carriers (e.g. latex particles), capsular carriers and vesicular carriers. A carrier having a shape suitable for a measurement method may be selected. Liposomes (single-layer or multilayer lipid films) and the like may also be used as the carrier for immobilizing the antibody thereon.

For binding the antibody to the carrier, there may be employed conventional methods such as physical adsorption method, ionic binding method, covalent binding method, and entrapping method [see, for example, Ichiro Chihata "Koteika Koso", Kodansha K. K. (Mar. 20, 1975)]. In particular, the physical adsorption method is preferable because of its simplicity. The antibody may be bound to the carrier either directly or through another substance between them.

As a labeling agent for preparing the labeled antibody, there may be used, for example, radioisotopes (e.g. 32P, 3H, 14C and 125I), enzymes (e.g. β-galactosidase, peroxidase, alkaline phosphatase, glucose-6-phosphate dehydrogenase, catalase, glucose oxidase, lactate oxidase, alcohol oxidase and monoamine oxidase), coenzymes·prosthetic groups (e.g. FAD, FMN, ATP, biotin and heme), fluorescein derivatives (e.g. fluorescein isothiocyanate and fluorescein thiofulvamyl), Rhodamine derivatives (e.g. tetramethyl Rhodamine B isothiocyanate), fluorescent dyes such as umbelliferone and 1-anilino-8-naphthalenesulfonic acid, luminol derivatives (e.g. luminol, isoluminol and N-(6-aminohexyl)-N-ethylisoluminol), and colloidal metal particles of gold, silver, platinum, a compound or any of these metals, or the like.

A method for binding the labeling agent to the antibody may be properly selected from conventional methods as described in text books [e.g. "Zoku Seikagaku Jikken Koza 5, Men-eki Seikagaku Kenkyuho", Tokyo Kagaku Dojin K. K., pp. 102–112 (1986)].

(2) Detection kit

The detection kit of the present invention is used in a method for detecting dissecting aortic aneurysm which comprises measuring smooth muscle myosin heavy chain in a test sample according to immunoassay, and detecting dissecting aortic aneurysm on the basis of the value obtained. Therefore, the kit is characterized by comprising at least the above-mentioned antibody reagent of the present invention as a constituent reagent and a surfactant-containing washing solution added thereto as another constituent reagent.

As the antibody reagent in the detection kit of the present invention, an antibody reagent having a shape suitable for an immunoassay method adopted in the kit (e.g. an immobilized antibody or a labeled antibody) may be properly selected from the above-exemplified antibody reagents and incorporated into the kit.

The surfactant contained in the washing solution is not particularly limited so long as it is water-soluble. In particular, an amphoteric surfactant or a nonionic surfactant is preferable. A specific example of the amphoteric surfactant is egg yolk lysolecithin. Specific examples of nonionic surfactant are Tween series surfactants (e.g. Tween 20, Tween 40, Tween 60, Tween 80 and Tween 85), Span series surfactants (e.g. Span 20, Span 80, Span 85 and Span 80), Brij series surfactants (e.g. Brij 35 and Brij 58), and (n) p-t-octyl phenyl ether series surfactants (e.g. Triton CF-10, Triton N-101, Triton X-100, Triton X-114, Triton X-305, Triton X-405 and Nonidet P-40). The amount of the surfactant added is suitably 0.003% (w/v) or more.

The washing solution containing such a surfactant is incorporated into the detection kit of the present invention and used in the assay, whereby smooth muscle myosin heavy chain in a sample can be measured with higher sensitivity.

As reagents other than those described above, reagents suitable for a measurement system may be properly selected from those usually used in the assay method (e.g. standard antigen solutions, an enzyme solution, substrate solution, reaction-stopping solution, and diluent for sample) and may be incorporated into the detection kit.

The assay method adopted in the detection kit of the present invention is not particularly limited so long as it is a conventional method adopted in immunoassay. There may be adopted any assay method such as competitive method, sandwich method, agglutination method, blot overlay method, immunochromatograph method and the like.

The details of the assay method adopted is referred to, for example, the following articles:

(a) Hiroshi Irie "Radioimmunoassay, second series", Kodansha K. K. (May 1, 1979);
(b) Eiji Ishikawa, et al. "Koso Men-eki Sokuteiho" 2nd. ed., IGAKU SHOIN Ltd. (Dec. 15, 1982);
(c) "Immunoassay for Clinical Examinations—Techniques and Application", Rinsho Byori, extra issue, special edition No. 53, Rinsho Byori Kankokai (1983);
(d) "Cyclopedia of Biotechnology", CMC K. K. (Oct. 9, 1986);
(e) JP-B 6-43998, JP-A 55-15100, JP-B 7-60159 and JP-A 63-25553;
(f) "Methods in ENZYMOLOGY Vol. 70" (Immunochemical techniques (Part A));
(g) "Methods in ENZYMOLOGY Vol. 73" (Immunochemical techniques (Part B));

(h) "Methods in ENZYMOLOGY Vol. 74" (Immunochemical techniques (Part C));
(i) "Methods in ENZYMOLOGY Vol. 84" (Immunochemical techniques (Part D: Selected Immunoassay)); and
(j) "Methods in ENZYMOLOGY Vol. 92" (Immunochemical techniques (Part E: Monoclonal Antibodies and General Immunoassay Methods)).
(the articles (f) to (j) are published by Academic Press).

The detection kit of the present invention is further explained below by taking the case of sandwich method which is a suitable method among assay methods. As the kit, the following kit may be exemplified.

Kit A:
① immobilized first antibody;
② second antibody;
③ labeled anti-immunoglobulin antibody;
④ antigen of a known concentration; and
⑤ washing solution (containing a surfactant).

Labeled second antibody may be used in place of both the second antibody and the labeled anti-immunoglobulin antibody of kit A. As such a kit, the following kit B is exemplified.

Kit B:
① immobilized first antibody;
② labeled second antibody;
③ antigen of a known concentration; and
④ washing solution (containing a surfactant).

A kit comprising such constituent reagents is suitable for, for example, rapid assay for obtaining measurement results within one hour.

In addition, when biotin-avidin method is employed, the following kit C is exemplified.

Kit C:
① immobilized first antibody;
② biotinylated second antibody;
③ labeled avidin;
④ antigen of a known concentration; and
⑤ washing solution (containing a surfactant).

In the above-mentioned kits, needless to say, the term "antibody" means an antibody to smooth muscle myosin heavy chain, and the term "antigen" means smooth muscle myosin heavy chain. The first antibody and the second antibody may be capable of recognizing either the same antigenic determinant or different antigenic determinant on smooth muscle myosin heavy chain.

A method for measuring smooth muscle myosin heavy chain in a test sample using any of the above-mentioned detection kits is not different at all from those adopted in the case of using other conventional detection kits in which sandwich method is employed. In detail, an immobilized antibody reagent is reacted with the test sample, and B/F separation is carried out if necessary, after which a labeled antibody reagent is reacted with the reaction product (two-step method). Alternatively, an immobilized antibody reagent, the test sample and a labeled antibody reagent are reacted at the same time (one-step method). In either case, after the reaction(s), smooth muscle myosin heavy chain in the sample may be detected or quantitated by a conventional method suitable for a labeling agent used for preparing the labeled antibody.

(3) Detection method

The detection method of the present invention comprises measuring smooth muscle myosin heavy chain in a test sample, and detecting dissecting aortic aneurysm on the basis of the value obtained.

The test sample used for the measurement is blood collected (with the lapse of time) from a patient suspected of suffering from dissecting aortic aneurysm, namely, a patient complaining of chest pain, or a fraction obtained by fractionating the blood (e.g. serum). If necessary, the test sample may be used in the measurement after having been diluted with a suitable buffer solution such as PBS.

It is sufficient that smooth muscle myosin heavy chain in a blood sample is detected or quantitated using the above-mentioned antibody reagent or detection kit of the present invention.

When it is revealed as a result of the measurement that the smooth muscle myosin heavy chain level in the blood sample is significantly higher than the smooth muscle myosin heavy chain average level in blood from normal individuals, it is diagnosed that the patient from whom the blood sample has been collected may be suffering from dissecting aortic aneurysm with a very high probability, and the patient should be subjected to more detailed examinations. When the smooth muscle myosin heavy chain level in the blood sample is not statistically different from that of blood from normal individuals, it is diagnosed that the patient from whom the blood sample has been collected is highly likely to be free from dissecting aortic aneurysm, and the patient should be subjected to reexaminations from a different viewpoint.

EXAMPLES

The present invention is specifically illustrated with the following examples, which should not be construed as limiting the scope of the invention.

Example 1

Preparation of Various Kinds of Myosins

Human uterus smooth muscle myosin, human aorta smooth muscle myosin, human platelet myosin and human skeletal muscle myosin were provided by Dr. Matsumura (Saga Medical School). Human cardiac muscle myosin was purified according to the method of Yazaki (Circ. Res., 36:208, 1975). The purity of these myosins was assessed by SDS-PAGE, after which the protein were quantatively determined according to the method of Lowry (J. Biol. Chem., 193:265–275, 1951) with bovine serum albumin as a standard. All the myosins were composed of heavy chain and light chain.

Example 2

Preparation of Monoclonal Antibodies

1) Preparation of monoclonal antibody-producing hybridomas

BALB/c mice aged 6 to 8 weeks were immunized intraperitoneally with 25 to 50 µg of human uterus smooth muscle myosin emulsified with complete Freund's adjuvant, 4 to 7 times at 2- to 4-week interval. After the final immunization, the mouse with highest titer was given intravenously 10 µg of human uterus smooth muscle myosin in saline.

Three days after the final immunization, the spleen was removed from this mouse, and splenocytes in the spleen were mixed with mouse myeloma cells [P3-X63-Ag8-U1 (P3U1) (ATCC CRL-1597) in the ratio of 10:1. The resulting mixture was centrifuged to obtain pellets, to which 1 ml of a RPMI1640 solution containing 50% polyethylene glycol was slowly added to carry out cell fusion. Thereto was further added RPMI1640 medium to make a total volume of 10 ml, followed by centrifugation. The pellets thus obtained were resuspended in RPMI1640 medium containing 10% fetal calf serum (FCS) so that the cell density of P3U1 might be 3×10⁴ cells/0.1 ml, and the suspension was dispensed in 0.1 ml aliquots into a 96-well microtiter plate.

After 24 hours, 0.1 ml of HAT medium was added to each well, after which one-half of the medium in each well was replaced by fresh HAT medium every 3 to 4 days.

On the 7 to 10th day after the cell fusion, the culture supernatant was sampled and dispensed in 50 µl aliquots into a 96-well polyvinyl chloride (PVC) plate previously coated with human uterus smooth muscle myosin and blocked with 3% gelatin, and was incubated at room temperature for 1 hour. After washing the plate three times with PBS, a solution prepared by diluting biotinylated horse anti-mouse IgG (Vector Laboratories) in 500-fold with PBS containing 1% bovine serum albumin (BSA) was dispensed in 50 µl aliquots into each well in the plate and allowed to stand at room temperature for 1 hour. After washing three times with PBS, a solution prepared by diluting peroxidase-avidin D (Vector Laboratories) in 2000-fold with PBS containing 1% BSA was dispensed in 50 µl aliquots into each well in the plate and allowed to stand at room temperature for 15 minutes. After washing three times with PBS, 200 µl of a substrate solution (containing 0.25 mg/ml of 4-aminoantipyrine, 0.25 mg/ml of phenol and 0.4 M of hydrogen peroxide) was added, and the reaction solution was subjected to coloration at room temperature. Absorbance at 550 nm was measured by means of a microplate photometer, and on the basis of the value obtained, hybridomas producing a monoclonal antibody which is reactive specifically with human uterus smooth muscle myosin were selected.

The hybridoma cells thus selected were cloned by limiting dilution to establish 5 clones of hybridoma (1H6, 4E12, 9A12, 9D7 and 10G2) capable of producing an antibody to human uterus smooth muscle myosin. Of these, hybridoma 1H6 and hybridoma 4E12 were deposited as SMHMW1H6 and SMHMW4E12 under the Budapest Treaty, respectively, in Bioengineering Research Institute, Agency of Industrial Science and Technology, Ministry of International Trade and Industry, and given Accession Numbers FERM BP-4829 and FERM BP-4830, respectively, under the date of Oct. 13, 1994.

In the above experiment, the proportion of the desired monoclonal antibody-producing hybridomas obtained relative to the number of wells is as shown in Table 1.

TABLE 1

Proportion of monoclonal antibody-producing hybridomas

| Number of wells positive to specific antibody | Number of wells containing proliferated cells | Total number of wells |
|---|---|---|
| 11 | 653 | 940 |

2) Preparation and purification of monoclonal antibodies

Next, cells of each clone established were cultured and then intraperitoneally administered to mice previously given pristane, in a number of 3×10⁶ per mouse. After about 2 weeks, 5 ml of ascitic fluid was collected from each mouse.

A mixture of the ascitic fluid and an equal volume of 1.5 M glycine-HCl buffer (pH 8.9) containing 3 M sodium chloride was passed through a Protein A Sepharose CL-4B column (Pharmacia Fine Chemicals) which had been equilibrated with the same glycine-HCl buffer as above. After washing the column with a sufficient volume of the same glycine-HCl buffer as above, antibody was eluted with 0.1 M citrate buffer (pH 6.0). The eluate was dialyzed against PBS and the purity of the antibody was confirmed according to SDS-polyacrylamide gel electrophoresis (SDS-PAGE), whereby a purified monoclonal antibody was obtained.

Example 3

Properties of Monoclonal Antibodies

1) Isotype

A culture supernatant of each hybridoma was added to a 96-well PVC plate previously coated with human uterus smooth muscle myosin and blocked with 3% gelatin, and the antibody was screened for isotype using a MonoAb-ID EIA kit (Zymed Laboratories).

The results are as shown in Table 2.

TABLE 2

Isotypes of monoclonal antibodies

| Hybridoma | 1H6 | 4E12 | 9A12 | 9D7 | 10G2 |
|---|---|---|---|---|---|
| Isotype | IgG1/κ | IgG1/κ | IgG1/κ | IgG1/κ | IgG1/κ |

2) Analysis for specificity by Western blotting

Each monoclonal antibody was analyzed for specificity according to Western blotting.

Human uterus smooth muscle myosin (1 mg/ml) was heat-treated at 100° C. for 5 minutes together with an equal amount of a reducing solution. The thus treated protein was subjected to SDS-PAGE by means of a mini-gel electrophoresis apparatus (Marysol K. K.) at 10 mV for about 3 hours using a 10% separating gel and a 5% stacking gel. Blotting was carried out as follows. The protein was transferred to a nitrocellulose membrane by means of a blotting apparatus for mini-gel (Marysol K. K.) by electrical current supply at 37 V for about 18 hours. The nitrocellulose membrane was cut into strips along the migration lines and some of them were subjected to protein staining with Amid black. The other strips were blocked with 3% gelatin and subjected to reaction with a culture supernatant of each hybridoma at room temperature for 1 hour.

These strips were washed twice with 20 mM Tris-500 mM NaCl buffer (pH 7.5) containing 0.05% Tween 20 (T-TBS) for 10 minutes, and then subjected to reaction with a 1/500 dilution of biotinylated horse anti-mouse IgG (Vector Laboratories) at room temperature for 1 hour. Thereafter, the strips were washed twice with T-TBS for 10 minutes and then subjected to reaction with a 1/2000 dilution of peroxidase-avidin D (Vector Laboratories) at room temperature for 15 minutes. Subsequently, the strips were washed twice with T-TBS for 10 minutes, subjected to coloration with a color development solution containing 30 mg of HRP color development reagent (Bio-Rad Laboratories), 10 ml of methanol, 50 ml of TBS and 30 µl of a 30% aqueous hydrogen peroxide solution, and then washed with distilled water.

As a result of the protein staining with Amid black, there were observed five bands of 200 K (uterus smooth muscle myosin heavy chain), 140 K (a fragment of uterus smooth muscle myosin heavy chain), 70 K (a fragment of uterus smooth muscle myosin heavy chain), 20 K (uterus smooth muscle myosin light chain) and 17 K (uterus smooth muscle myosin light chain).

According to Western blotting, it was confirmed that all the monoclonal antibodies react with human uterus smooth muscle myosin heavy chain, but that none of them react with human uterus smooth muscle myosin light chains.

Example 4

Detection Kit in Sandwich Method

1) Preparation of biotinylated antibodies

Each of the above-mentioned monoclonal antibodies was dialyzed against a 0.1 M sodium hydrogencarbonate solution, and the dialyzed solution was concentrated to 2 mg/ml with Centriflow (Amicon). Biotin (long arm) NHS reagent (Vector Laboratories) was dissolved in dimethylformamide to a concentration of 10 mg/ml, after which 20 μl of the dilution was mixed with 1 ml of the above-mentioned antibody solution, and the reaction was carried out at room temperature for 2 hours. The reaction was terminated with 5 μl of ethanolamine, and the reaction solution was dialyzed twice against PBS to obtain a biotinylated antibody. The biotinylated antibody was diluted to 1 μg/ml with PBS containing 1% BSA, to obtain a biotinylated antibody solution.

2) Preparation of immobilized antibody

The anti-(smooth muscle myosin heavy chain) monoclonal antibody (4E12) was diluted to 10 μg/ml with PBS, and the dilution was dispensed in 50 μl aliquots into a 96-well plate (H type, Sumitomo Bakelite Co., Ltd.) and allowed to stand overnight at 4° C. The plate was washed three times with PBS containing 0.05% Tween 20, after which 0.5% skim milk was dispensed thereinto in 300 μl aliquots, and the plate was allowed to stand at room temperature for 1 hour. The skim milk solution was removed to obtain an immobilized antibody reagent.

3) Preparation of other reagents and a kit

Smooth muscle myosin heavy chain standard solutions

The standard solutions were prepared by diluting human aorta smooth muscle myosin to a concentration of 25, 12.5, 6.25, 3.125, 1.563, 0.781 or 0.391 ng/ml in terms of the heavy chain with PBS containing 1% BSA.

Washing solution

The solution was prepared by dissolving Tween 20 in PBS to a concentration of 0.05% (w/v).

Enzyme-labeled avidin solution

The avidin solution was prepared by diluting peroxidase-labeled avidin D (A-2004, Vector Laboratories) in 5,000-fold with PBS containing 1% BSA.

Substrate solution

The solution was prepared by dissolving 3,3',5,5'-tetramethylbenzidine dihydrochloride (TMBZ) and hydrogen peroxide in 0.2 M citrate buffer (pH 3.8) to concentrations of 0.3 mM and 0.005%, respectively.

Enzyme reaction stopping solution 1N sulfuric acid was used.

The above-mentioned reagents were combined into a kit, whereby the detection kit of the present invention was prepared.

Example 5

1) Calibration curve

To each well containing the immobilized antibody reagent (4E12) was fed 100 μl of PBS containing 1% BSA and then 50 μl of each smooth muscle myosin heavy chain standard solution, and stirred, followed by standing at room temperature for 4 hours. Each well was washed three times with the washing solution, fed with 50 μl of the biotinylated antibody (1H6) solution, and then allowed to stand at room temperature for 30 minutes. Thereafter, each well was washed three times with the washing solution, fed with 50 μl of the enzyme-labeled avidin solution, and then allowed to stand at room temperature for 15 minutes. Subsequently, each well was washed three times with the washing solution, fed with 100 μl of the substrate solution, and then allowed to stand at room temperature for 10 minutes, whereby a color was developed. The reaction was stopped by adding 100 μl of the enzyme reaction stopping solution to each well, and absorbance at 450 nm was measured with a microplate photometer. The calibration curve thus obtained is shown in FIG. 1.

2) Effect of surfactants

As a result of investigating the concentration of Tween 20 in the washing solution in the procedure described in 1) above, it was proved that the measuring sensitivity can be markedly enhanced at a concentration of 0.003% (w/v) or more.

Effect of various surfactants other than Tween 20 was compared with that of Tween 20. In detail, washing solutions were prepared by dissolving each of the various surfactants in PBS to a concentration of 0.05% (w/v), and by the use of each washing solution, calibration curves were obtained in the same manner as above. As a result, it was found that as shown in FIGS. 3 to 7, the presence of any of amphoteric surfactants and nonionic surfactants in the washing solutions brings about a marked effect as in the case of Tween 20.

3) Reproducibility

Figure 3:
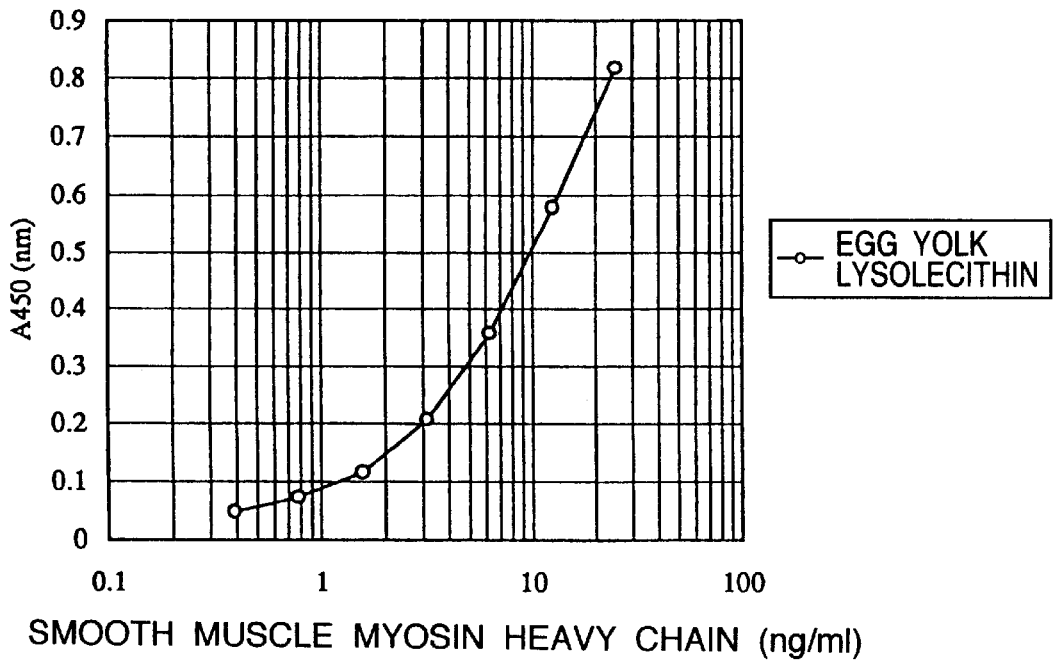
Figure 4:
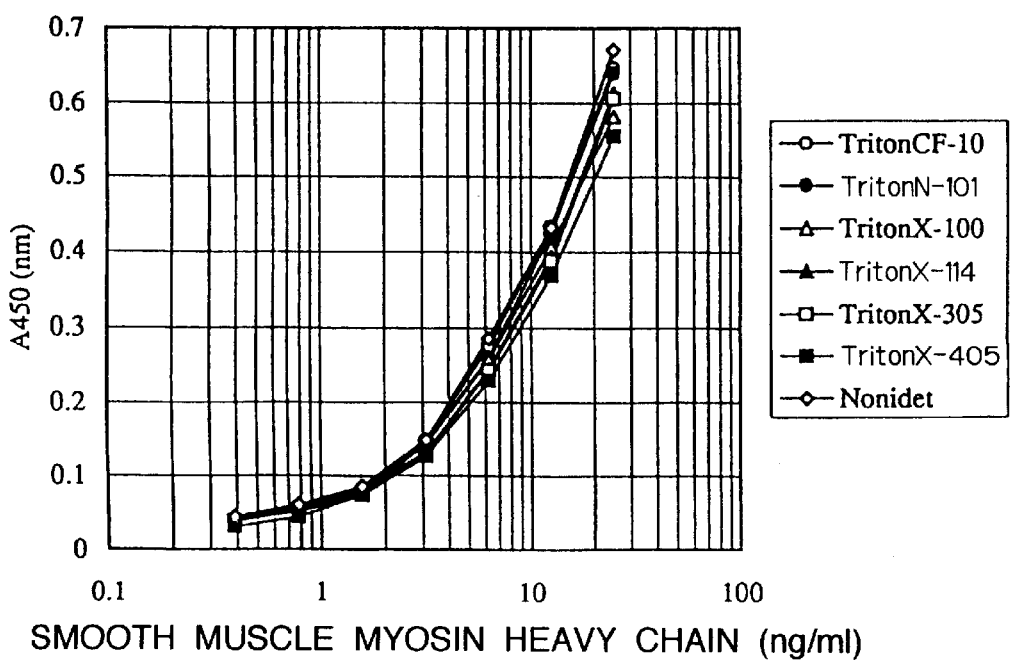
Figure 5:
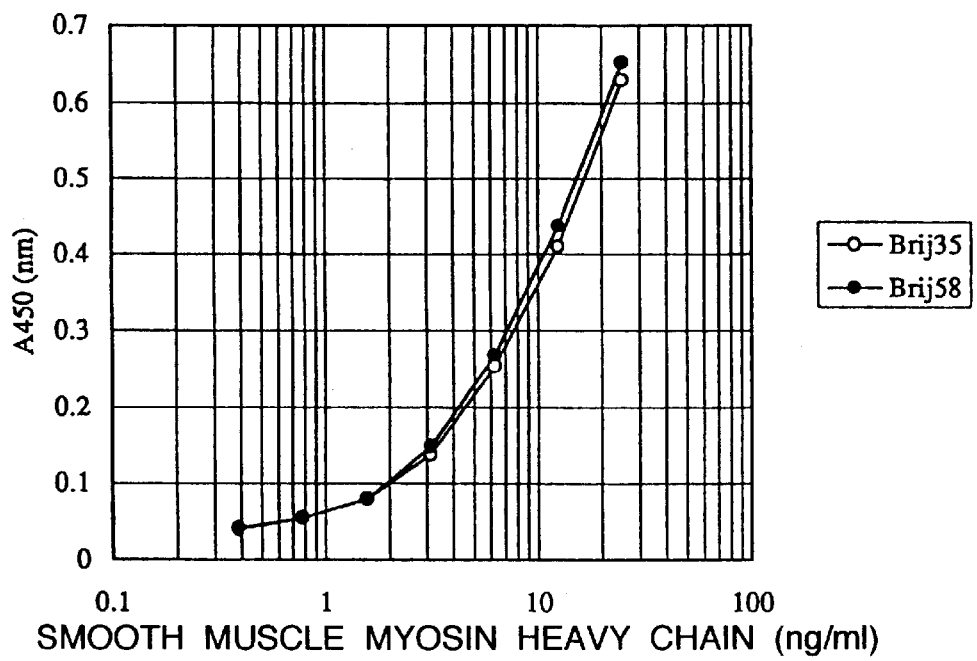
Figure 6:
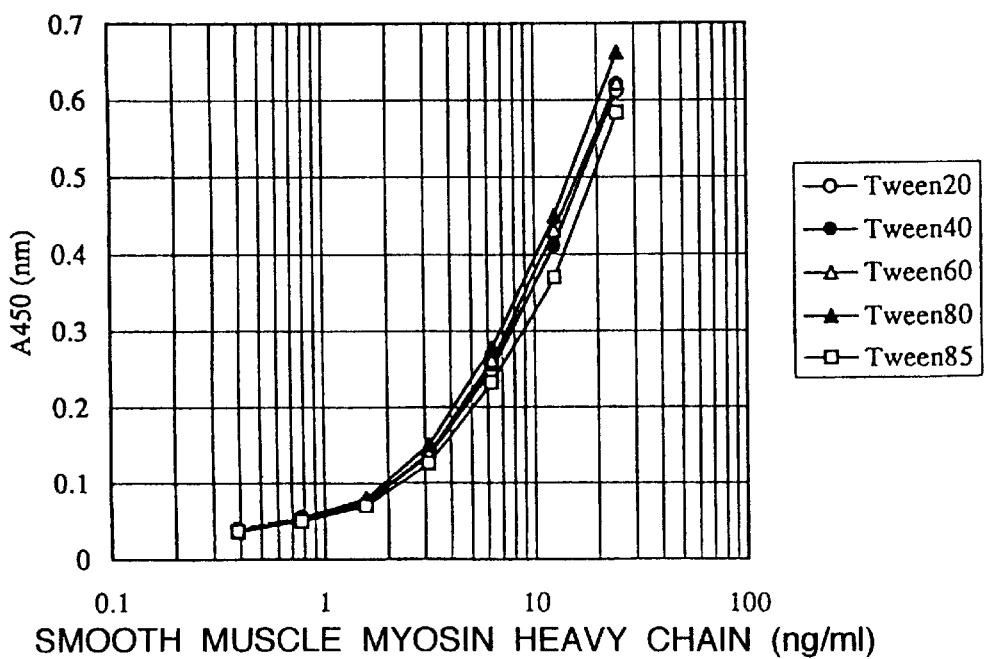
Figure 7:
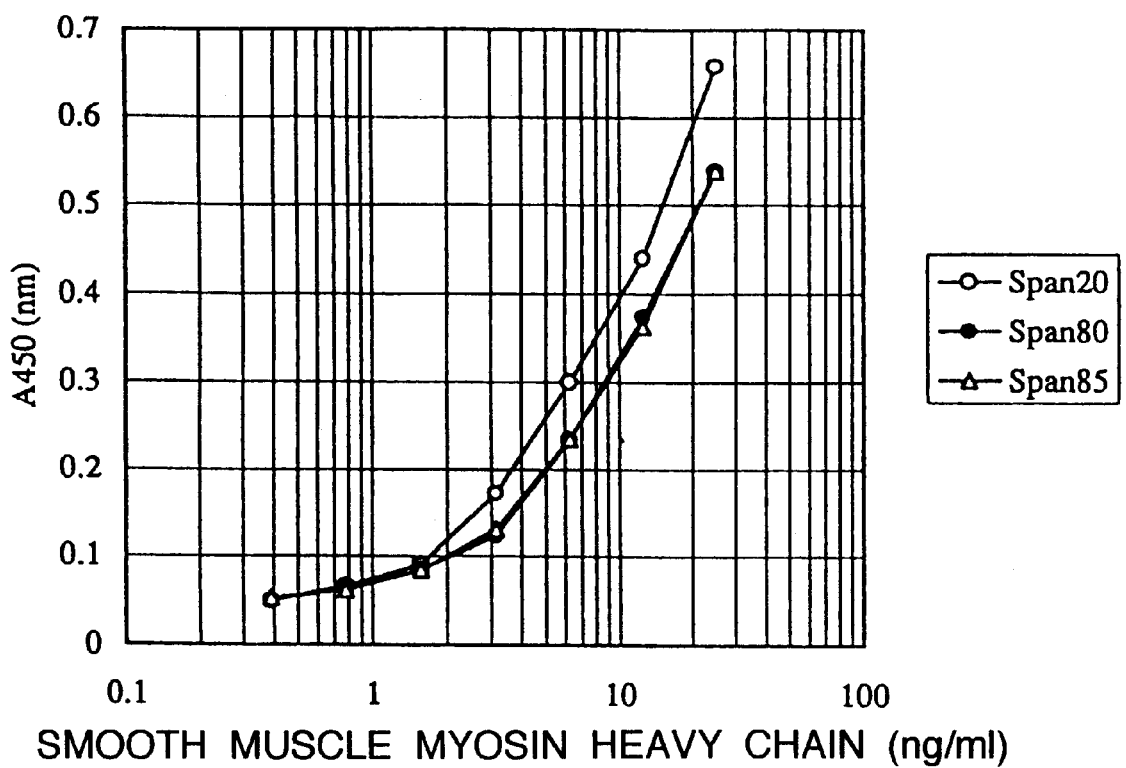

Using three samples (A, B and C), within-run reproducibility and between-day reproducibility were investigated according to the procedure as described in 1) above. As a result, it was found that as shown in FIGS. 3 and 4, CV values less than 10% are obtained in the case of both reproducibilities, namely, it was proved that the assay shows good reproducibility.

TABLE 3

Within-run reproducibility

| | | Measured value ng/ml | Mean ng/ml | SD | CV % |
|---|---|---|---|---|---|
| A | 1 | 1.4 | 1.3 | 0.1 | 6.5 |
| | 2 | 1.3 | | | |
| | 3 | 1.2 | | | |
| | 4 | 1.3 | | | |
| | 5 | 1.2 | | | |
| B | 1 | 4.9 | 5.2 | 0.2 | 4.6 |
| | 2 | 5.0 | | | |
| | 3 | 5.1 | | | |
| | 4 | 5.5 | | | |
| | 5 | 5.3 | | | |
| C | 1 | 16.0 | 15.9 | 0.2 | 1.1 |
| | 2 | 15.8 | | | |
| | 3 | 16.2 | | | |
| | 4 | 15.8 | | | |
| | 5 | 15.8 | | | |

TABLE 4

Between-day Reproducibility

| | | Measured value ng/ml | Mean ng/ml | SD | CV % |
|---|---|---|---|---|---|
| A | 1 | 1.1 | 1.1 | 0.1 | 4.9 |
| | 2 | 1.1 | | | |
| | 3 | 1.2 | | | |
| | 4 | 1.2 | | | |
| | 5 | 1.1 | | | |
| B | 1 | 5.0 | 5.2 | 0.2 | 4.6 |
| | 2 | 5.1 | | | |
| | 3 | 5.6 | | | |
| | 4 | 5.3 | | | |
| | 5 | 5.0 | | | |
| C | 1 | 14.0 | 15.8 | 1.1 | 6.9 |

TABLE 4-continued

Between-day Reproducibility

| | Measured value ng/ml | Mean ng/ml | SD | CV % |
|---|---|---|---|---|
| 2 | 15.9 | | | |
| 3 | 16.8 | | | |
| 4 | 15.5 | | | |
| 5 | 16.6 | | | |

4) Dilution linearity

Figure 8:
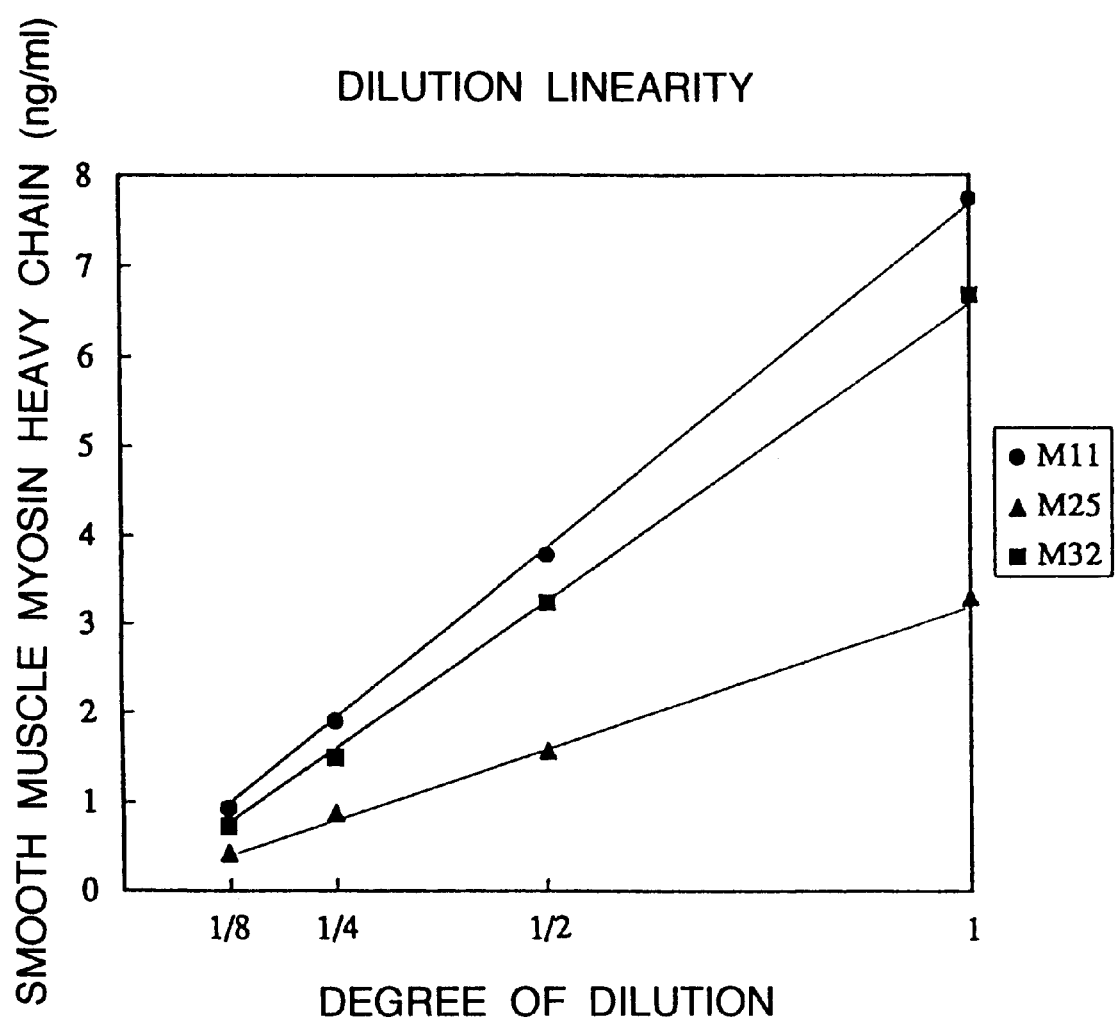
FIG. 8 shows the results of investigating dilution linearity.

According to the procedure as described in 1) above, the sera of three patients (M11, M25 and M32) were diluted with the standard solution (0 ng/ml), and the dilution linearity was investigated to reveal that as shown in FIG. 8, lines obtained in all the cases are linear those starting from the zero point. Thus, it was made clear that good dilution linearity can be attained.

5) Addition and recovery

According to the procedure as described in 1) above, the standard solutions were added to the sera of patients (samples M14 and M24), and the recovery of smooth muscle myosin heavy chain was investigated to reveal that as shown in Table 5, smooth muscle myosin heavy chain can be recovered in an amount which is substantially the same as the adding amount.

TABLE 5

Addition-and-recovery test

| Sample | Added (ng/ml) | Observed (ng/ml) | Recovery (ng/ml) | Recovery (%) |
|---|---|---|---|---|
| M14 | 0.0 | 2.4 | | |
| | 1.3 | 3.5 | 1.1 | 89.8 |
| | 5.0 | 7.2 | 4.8 | 95.7 |
| | 20.0 | 18.7 | 16.3 | 81.5 |
| M24 | 0.0 | 1.8 | | |
| | 1.3 | 3.0 | 1.2 | 96.3 |
| | 5.0 | 7.0 | 5.3 | 105.3 |
| | 20.0 | 18.6 | 16.9 | 84.3 |

6) Cross-reactivity

Figure 9:
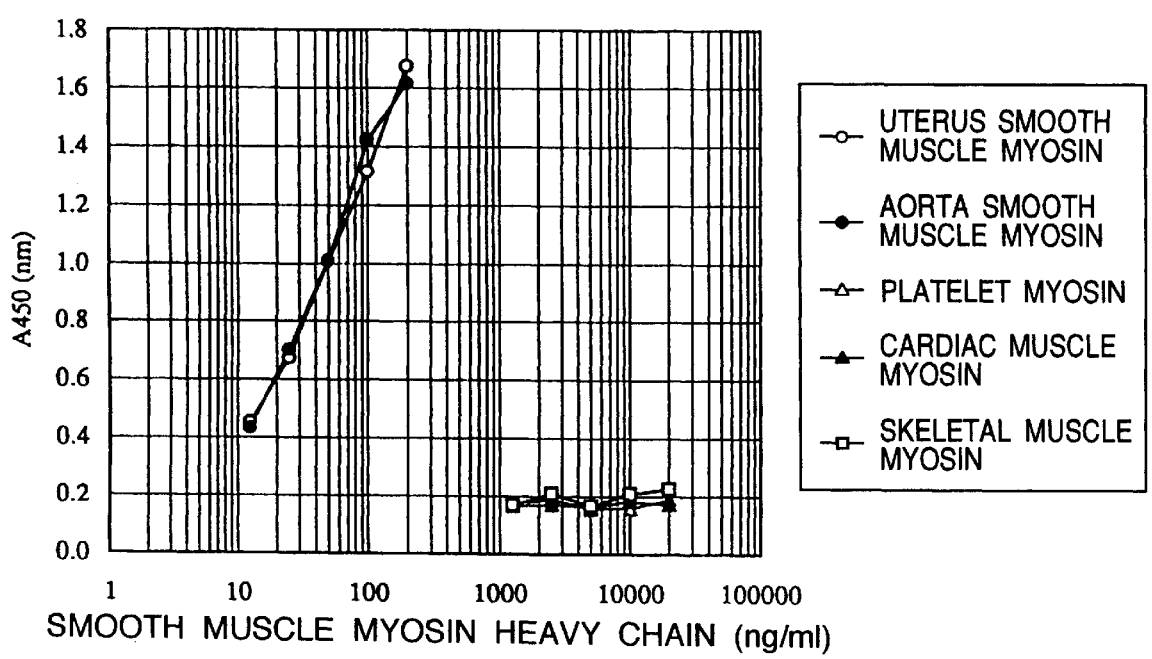
FIG. 9 shows the results of investigating cross-reactivity.

Cross-reactivity with various myosins was investigated according to the procedure as described in 1) above. As a result, it was confirmed that as shown in FIG. 9, the monoclonal antibodies react with uterus smooth muscle myosin similarly with aorta smooth muscle myosin but hardly react with any of skeletal muscle myosin, cardiac muscle myosin and platelet myosin (non-muscle myosin).

7) Measurement in sera of healthy individuals

The smooth muscle myosin heavy chain levels in the sera of 75 normal individuals were measured according to the procedure as described in 1) above to reveal that the mean thereof was 0.9 ng/ml and the standard deviation 0.9 ng/ml.

8) Measurement in sera of patients

Figure 10:
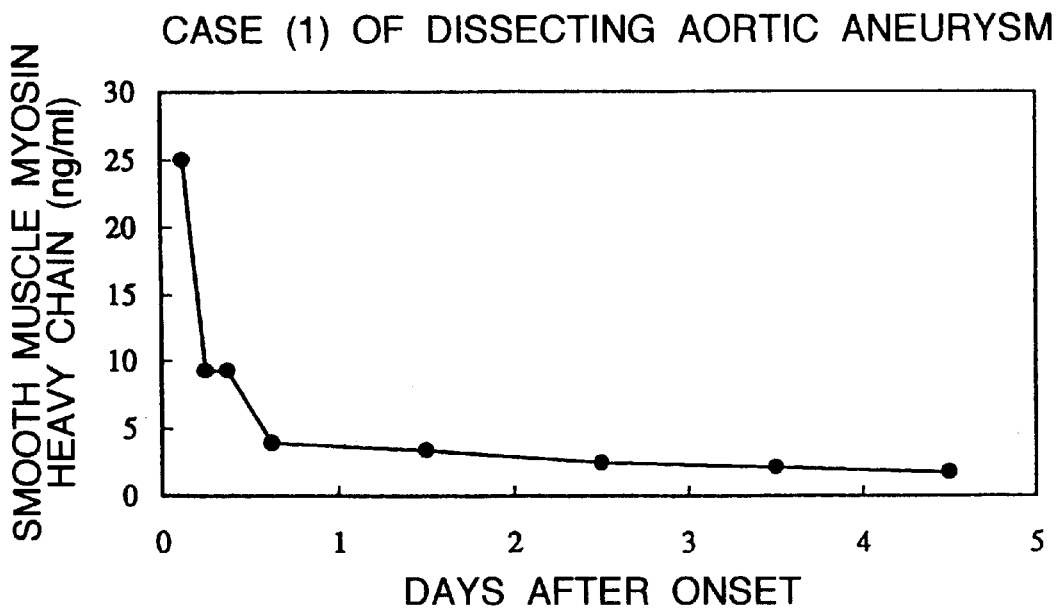
FIG. 10 shows the results of measuring smooth muscle myosin heavy chain in the serum of a patient.
Figure 11:
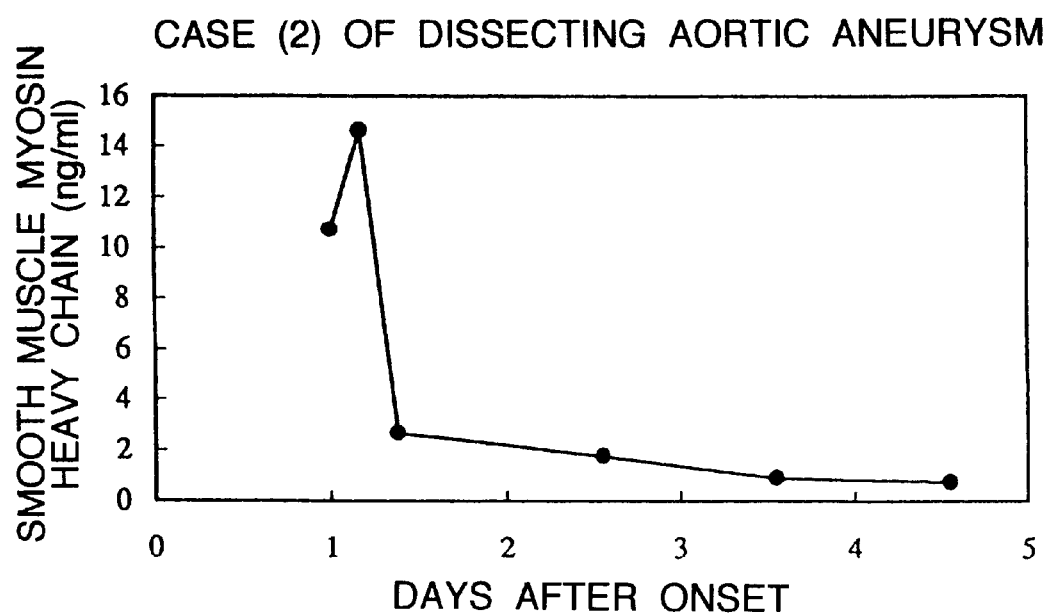
FIG. 11 shows the results of measuring smooth muscle myosin heavy chain in the serum of a patient.

According to the procedure as described in 1) above, there was measured the smooth muscle myosin heavy chain level in each of serum samples collected from two patients with dissecting aortic aneurysm with the lapse of time from the onset of the disease. As a result, marked elevation of the smooth muscle myosin heavy chain level was confirmed at the onset of the disease as shown in FIGS. 10 and 11, indicating that the measurement of smooth muscle myosin heavy chain is useful for detection or diagnosis of dissecting aortic aneurysm. In this case, confirmative diagnosis of dissecting aortic aneurysm was conducted by operation.

INDUSTRIAL AVAILABILITY

The present inventors found for the first time that dissecting aortic aneurysm can be detected by measuring smooth muscle myosin heavy chain in a test sample. Moreover, since immunoassay is employed as a detection method in the present invention, the method of the present invention does not require any special equipment and is applicable to urgent examination for dissecting aortic aneurysm, unlike conventional methods.

In addition, the antibody reagent and detection kit of the present invention are absolutely necessary for practicing the detection method of the present invention. Furthermore, when there are used at least one monoclonal antibody and a washing solution containing a specific surfactant, smooth muscle myosin heavy chain in a test sample can be detected with higher sensitivity, so that the detection method of the present invention is applicable to not only the urgent examination but also progress observation during and after treatment.

We claim:

1. A method for detecting dissecting aortic aneurysm or aortic dissection in a patient suspected of having dissecting aortic aneurysm or aortic dissection comprising:

obtaining a sample of blood, plasma, or serum from said patient;

reacting said sample with an antibody specific for smooth muscle myosin heavy chain in order to form an amount of complex between said antibody and any smooth muscle myosin heavy chain present in the sample;

detecting the amount of complex formed in the reacting step as an indication of an amount of the smooth muscle myosin heavy chain present in the sample, wherein an elevated amount of the smooth muscle myosin heavy chain present in the sample in comparison to amounts of smooth muscle myosin heavy chain detected in normal samples indicates dissecting aortic aneurysm or aortic dissection in the patient.

2. The method of claim 1 in which said antibody is monoclonal.

3. The method of claim 1, in which the method is a sandwich immunoassay.

4. The method of claim 1 in which said antibody is immobilized on a solid phase to immobilize said complex formed in the reacting step, and said amount of immobilized complex formed in the reacting step is indicated by, after washing the immobilized complex with a surfactant-containing washing solution, detecting an amount of binding of a labelled second antibody specific for smooth muscle myosin heavy chain to said immobilized complex.

5. The method of claim 4 in which the surfactant is selected from the group consisting of amphoteric surfactant and nonionic surfactant.

6. The method of claim 4 in which one or both of said antibody or second antibody are monoclonal antibodies.

* * * * *